United States Patent [19]

Eby, III

[11] Patent Number: 5,095,035
[45] Date of Patent: Mar. 10, 1992

[54] FLAVOR STABLE ZINC ACETATE COMPOSITIONS FOR ORAL ABSORPTION

[76] Inventor: George A. Eby, III, 2109 Paramount Ave., Austin, Tex. 78704

[21] Appl. No.: 633,043

[22] Filed: Dec. 24, 1990

Related U.S. Application Data

[63] Continuation-in-part of Ser. No. 182,983, Apr. 18, 1988, Pat. No. 5,002,970, and a continuation-in-part of Ser. No. 102,750, Sep. 24, 1987, Pat. No. 4,956,385, which is a continuation of Ser. No. 667,097, Nov. 1, 1984, abandoned, which is a continuation-in-part of Ser. No. 378,479, May 14, 1982, Pat. No. 4,503,070, now Re. 33465, which is a continuation-in-part of Ser. No. 288,750, Jul. 31, 1981, abandoned, which is a continuation-in-part of Ser. No. 22,620, Jan. 5, 1981, abandoned.

[51] Int. Cl.$^5$ .................. A61K 9/10; A61K 9/68
[52] U.S. Cl. .................. 514/494; 514/974; 514/849; 514/888; 514/58; 514/777; 424/464; 424/58; 424/439; 424/440; 424/441; 424/442; 424/489; 424/641; 424/643
[58] Field of Search .............. 514/494, 974, 849, 888, 514/58, 777; 424/464, 58, 439, 440, 441, 442, 489, 641, 643

[56] References Cited

U.S. PATENT DOCUMENTS

| | | | |
|---|---|---|---|
| Re. 33,465 | 11/1990 | Eby | 514/494 |
| 153,421 | 7/1874 | Butts | 424/439 |
| 2,648,609 | 8/1953 | Wurster | 424/439 |
| 4,503,070 | 3/1985 | Eby | 514/494 |
| 4,684,528 | 8/1987 | Godfrey | 426/74 |
| 4,764,375 | 8/1988 | Paradissis | 424/439 |
| 4,766,004 | 8/1988 | Moskowitz | 424/439 |
| 4,777,162 | 10/1988 | Hijiya et al. | 424/439 |
| 4,794,014 | 12/1988 | Siren | 424/439 |
| 4,956,385 | 9/1990 | Eby, III | 424/439 |
| 4,980,169 | 12/1990 | Oppenheimer et al. | 424/439 |
| 5,002,970 | 3/1991 | Eby, III | 424/439 |

OTHER PUBLICATIONS

Failure of Zinc Acetate Lozenges to Alter the Course of Upper Respiratory Tract Infections in Australian Adults, by Douglas et al., Antimicrobial Agents and Chemotherapy, Aug. 1987, p. 1263.
Personal letter from R. M. Douglas to G. Eby dated Sep. 3, 87.
Personal letter from R. J. E. Williams to R. M. Douglas, Aug. 27, 87.
Reduction in Duration of Common Colds by Zinc Gluconate Lozenges . . . Eby et al., Aptimicrobial Agents and Chemotherapy, vol. 25, pp. 20-24, 1984.
Prophylaxis and Treatment of Rhinovirus Colds with zinc gluconate lozenges, by W. A. Nakib et al., Journal of Antimicrobial Chemotherapy, vol. 20, pp. 893-901, 1987.
Zinc and the Common Cold: Positive Findings in a Controlled Clinical Study Using a new Formulation by J. C. Godfrey et al. in 1991.
Two Randomized Controlled Trials of Zinc Gluconate Lozenge Therapy of Experimentally Induced Rhinovirus Colds by B. M. Farr in Antimicrobial Agents and Chemotherapy, 1987 vol. 131, p. 1183.

*Primary Examiner*—Ronald W. Griffin

[57] ABSTRACT

Thermally, chemically and flavor stable compositions for oral absorption by a human containing zinc acetate with a consumable, sweet pharmaceutical carrier and prepared in the form of a pleasant testing lozenge, powder, liquid or chewable composition for delivery of zinc to the oral and oral pharyngeal mucosa of a a human with said composition being absent the normal offensive aftertaste of zinc, and being primarily intended for use in treating common colds or in nutritional supplementation.

8 Claims, No Drawings

FLAVOR STABLE ZINC ACETATE COMPOSITIONS FOR ORAL ABSORPTION

This application is a continuation-in-part of applicant's copending application U.S. Ser. No. 07/182,983, filed Apr. 18, 1988, now U.S. Pat. No. 5,002,970 and a continuation-in-part of application U.S. Ser. No. 07/102,750, filed Sept. 24, 1987, now U.S. Pat. No. 4,956,385, which is a continuation of application Ser. No. 06/667,097, filed Nov. 1, 1984, now abandoned, which is a continuation-in-part application of Ser. No. 06/378,479, filed May 14, 1982, now U.S. Pat. No. 4,503,070, reissued on Nov. 27, 1990 as U.S. Pat. No. Re 33,465, which is a continuation-in-part application of U.S. Ser. No. 06/288,750, filed July 31, 1981, now abandoned which is a continuation-in-part application of U.S. Ser. No. 06/022,620, filed Jan. 5, 1981, now abandoned.

FIELD OF INVENTION

This invention relates to a method for masking flavor and aftertaste of compositions for oral absorption by humans which contain zinc acetate. More particularly, this invention relates to chemically, thermally and flavor stable compositions containing zinc acetate and pharmaceutically acceptable carriers including fructose, sugar and the like, with other necessary ingredients such as extra sweeteners, flavors, stabilizers and lubricants. Such compositions, when applied to oral and oral pharyngeal membranes of a human, are palatable and without undesirable taste or aftertaste yet allow oral and oral pharyngeal absorption of zinc ions.

GENERAL BACKGROUND

The art of managing metallic ions in food products has received much attention by the food industry. Metallic ions of iron, copper and zinc can be present in some food products with adverse effects on food integrity. If they are allowed to remain in some food products even in low concentrations, such metallic ions can greatly reduce shelf life of some fats, oils and other foods that are subject to spoiling and oxidization.

Chemical Sequestration of metallic ions: Sequestrants are chemicals that deactivate or stabilize these metallic ions by chemically typing up positively charged metal ions through chemical reactions to form stable, neutrally or negatively charged complexes that do not adversely affect integrity or quality of such food products. Sequestrants are also known as sequestering agents, stabilizers, chelators, chelating agents and metal scavengers. Sequestrants help to establish, maintain, and enhance integrity of many food products. From a food manufacturing viewpoint, sequestrants serve to stabilize or enhance numerous properties identified with wholesome food including color, flavor and texture. Usually, sequestrants chemically react with metallic ions to form complexes which, depending on stability of metal complexes, tend to alter properties and effects of metals in substrates. Many sequestrants employed in food production occur naturally in nature. They include as monocarboxylic acids gluconic and acetic acids which weakly sequester zinc ions; as hydroxycarboxylic acids citric and tartaric acids which strongly chelate zinc ions; as amino acids such as sweet tasting lysine, glycine, leucine, alanine, and valine; and various macromolecules such as porphyrins, peptides and proteins. Certain commercial sweeteners such as saccharin, sorbitol, mannitol and a constituent of aspartame, phenylalanine, have also been shown to bind with or sequester metals. For sequestration, chelation, to occur two general conditions must be met: (a) ligands must have proper steric and electronic configuration in relation to metal ions being complexed and (b) the surrounding milieu (pH, ionic strength, solubility, etc) must likewise be conductive to complex formation. That sequestration of metal ions is a desirable goal of food manufacturers is well known in the art.

Desirability of weak sequestration: However, desirability of strongly sequestering metal ions in all cases must be challenged in view of nature of some metal chelators relative to environments in which their use is intended. For example, use of zinc gluconate in lozenges and similar means has been described as a method for reducing duration of common cold symptoms (U.S. Pat. No. 4,503,070, Mar. 5, 1985 and its reissue U.S. Pat. No. Re 33,465). In such usage, zinc ions are only weakly bound by the gluconate moiety. The first stability constant of zinc gluconate is log $K_1$ 1.70. Thirty percent or more of zinc appears as positively charged zinc ions in acidic to neutral pHs, with remained being positively charged zinc gluconate. Such ions are available for those biochemical activities in oral and oral pharyngeal mucous membranes that result in a reduction in duration of common cold symptoms. Although the exact nature of biochemical activities of zinc ions in reducing duration of common cold symptoms remains to be determined, it is conclusive that zinc must be ionized. Published articles, "Reduction in Duration of Common Cold Symptoms by Zinc Gluconate Lozenges in a Double Blind Study", Antimicrobial Agents and Chemotherapy, 1984, 25(1), pp 20–24 by George A. Eby, et al and "Prophylaxis and Treatment of Rhinovirus Colds with Zinc Gluconate Lozenges", Journal of Antimicrobial Chemotherapy, 1987, 20(6), pp 893–901 by W. Al-Nakib, each used zinc gluconate either with no additional metal sequestrants added or with glycine added, and each showed a marked reduction in duration of common cold symptoms from positively charged zinc ions.

Adverse effects of sequestration: Conversely, in a similar study "Two Randomized Controlled Trials of Zinc Gluconate Lozenge Therapy of Experimentally Induced Rhinovirus Colds", Antimicrobial Agents and Chemotherapy, 1987 31(8) pp 1183–1187, by Barry M. Farr et al, citric acid, a strong zinc chelator, was used in lozenges in extramolar amounts sufficient to eliminate taste of zinc, resulting in no reduction in duration of common colds. The first stability constant of citric acid for zinc ions is generally accepted to be log $K_1$ 4.5. In oral use in lozenge form, zinc gluconate rapidly ionizes; as does zinc combined with other ligands having low stability constants, or other ligands that produce positively charged zinc ions such as glycine. It is known in the art that if such occurs in the presence of sufficient amount of a chelator having a high stability constants for zinc ions such as equimolar (or greater) citric acid, a new, vastly stronger equilibrium may occur. Such equilibrium may result in neutrally or negatively charged compounds having little or no bioavailability at salivary pH and normal oral tissue pH. In the case of lozenges containing zinc gluconate with extramolar citric acid, soluble zinc complexes were shown to be tasteless and were proposed to be sufficiently biologically available to be effective in reducing duration of common colds. However, with addition of extramolar citric acid, there occurs in saliva such powerful binding of zinc ions that negatively charged zinc species predominate. A complete loss of positively charged zinc ions in saliva and in oral tissues occurs. There is no metallic taste. No localized activity occurs, and no reduction in common cold duration occurs.

Stability of compositions containing zinc: In addition to the requirement that all ingredients in said compositions not adversely affect efficacy, ingredients must not adversely affect composition taste. They must be thermally, chemically and flavor stable under all normal conditions over long periods of time. This inventor conducted year-long laboratory tests of taste stability of hundreds of originally pleasant tasting, flavor masked zinc compositions. Various flavor masks, including glycine and anethole were tested. Glycine treated zinc gluconate under U.S. Pat. No. 4,684,528 was provided by the inventor, John C. Godfrey. Anethole has been discovered to be an aromatic flavor mask and aftertaste mask for all soluble and ionizable zinc compounds and is disclosed and claimed by George A. Eby III in U.S. patent application Ser. No. 182,983 dated Apr. 18, 1988, now U.S. Pat. No. 5,002,970, issued 3-26, 1991. All known sweet tablet bases such as sugar, dextrose, lactose, fructose, mannitol, sorbitol, xylitol and many other commercial products specifically designed for pharmaceutical tablets were tested with zinc compounds and flavor masks. Compositions kept in a closed un-air conditioned room were exposed to summer-time temperatures reaching 45 to 55 C. degrees. Glycine flavor masked zinc gluconate compositions in Mendell's Sugartab ® turned brown, apparently from high summer temperatures. Anethole (plated onto silica gel) flavor-asked zinc gluconate lozenge compositions of Sugartab ® lost most of their flavoring and became bitter with the highly objectionable aftertaste typically found with zinc gluconate and sucrose. Zinc gluconate with or without glycine did not adversely react or become bitter only in fructose lozenges. Flavors usually evaporated, suggesting that plating flavors on silica gel is inadequate for a flavor stable product, suggesting a need for spray dried flavors or flavor oil incorporated within cyclodextrins. Zinc acetate lozenges which originally contained anethole and other flavors, had no zinc aftertaste even if anethole had evaporated. Zinc acetate lozenges without anethole were not made. Said changes indicate that unexpected, undesired reactions occurred which are destructive to compositions. Such changes may inhibit commercial utility and preclude wide spread marketability of said compositions unless satisfactory solutions can be developed.

Other experiments: U.S. Pat. No. 4,684,528 shows that candy lozenges and various other oral compositions containing various zinc compounds, including zinc gluconate and zinc acetate, can be flavor masked with glycine and certain other amino acids. Amino acids found effective as a flavor mask and aftertaste mask are glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lycine, and D,L-lycine when molar ratio of said amino acids to zinc is from about 2 to 20. Importantly, said patent reveals that a zinc acetate formulation of hard candy without glycine had a sharp, undesirable taste and an unpleasant aftertaste.

The current need: In as much as there is an important need to develop thermally, chemically and flavor stable zinc lozenges and other means having a pleasant taste to introduce zinc ions into oral and oral pharyngeal mucous membranes primarily for treatment of common colds and nutritional supplementation; and in as much as serious mistakes taken from the prior art of taste management of zinc and other metallic ions have been made, particularly in the invention of thermally, chemically and flavor stable zinc lozenges for treating common colds; it is apparent that errors of the prior art must receive attention. A new way of eliminating objectionable taste and aftertaste of ionizable zinc compounds is needed using stable lozenge ingredients and new technology.

PRIMARY OBJECTIVE AND GENERAL DESCRIPTION OF INVENTION

Accordingly, it is a primary objective of this invention to disclose and claim an improved zinc composition that is thermally, chemically, and flavor stable, which effectively masks the flavor and aftertaste of zinc when intended to be absorbed into oral and oral pharyngeal mucous membranes, and especially when composition is for use in shortening duration of common colds or their symptoms, or for human nutritional support. These primary objectives and other objectives of this invention will be found apparent from the following general description and detailed examples.

Oral compositions of zinc generally: This invention relates to medicinal and nutritional compositions specifically containing zinc acetate and a sweet, consumable pharmaceutically acceptable carrier which is primarily intended to be used for absorption of zinc ion into oral and oral pharyngeal tissues of a human. As discovered from preceding cited thermal stability studies, compositions are without an objectionable aftertaste even without a flavor mask or added super sweetener. Compositions are chemically, thermally and flavor stable with no increase in bitterness. Although this invention primarily discloses and claims the discovery of aftertaste-free zinc acetate dispersed in a consumable pharmaceutically acceptable carrier; by necessity to clearly describe compositions, the invention fully describes said compositions as containing:

Zinc acetate in a consumable pharmaceutically acceptable carrier such as fructose, sugar, dextrose, maltose, lactose, sweetened water and the like, with following ingredients included as necessary:
(a) tablet binders for lozenges, troches and tablets such as polyethylene glycol,
(b) chewing gum base,
(c) soft candy ingredients,
(d) super sweeteners, such as saccharine,
(e) flavor oils such as methyl salicylate, menthol, eucalyptol,
(f) flavor masking oils such as anethole,
(g) stabilizers, such as beta cyclodextrins,
(h) tablet lubricants, and
(i) other pharmaceutical necessities
excluding amino acids disclosed in U.S. Pat. No. 4,684,528.

Such compositions include: solid forms such as tablets, troches, lozenges and powders; chewable forms such as chewing gums and soft candies; and liquids such as syrups, mouth washes and sprays. When said compositions are applied to oral and oral pharyngeal membranes of a human, they are palatable and without undesirable taste or unpleasant aftertaste yet allow oral and oral pharyngeal absorption of zinc ions.

Zinc acetate as source of zinc ions: Although zinc gluconate is the best known source of zinc and zinc ions for lozenges used in treating common colds, zinc acetate merits special attention. Zinc lozenges for treating common colds contain between 2 and 500 mg zinc (7 to 1679 mg zinc acetate) and more often contain about 2 to 50 mg of zinc (7 to 168 mg zinc acetate) and most often contain about 23 mg zinc. Zinc acetate offers improved, unexpected characteristics that require attention. That zinc acetate would be acceptable in zinc lozenges is very unexpected as zinc acetate has an extremely strong, vile taste completely offensive by any standard and much worse than the taste of zinc gluconate. It has chemical properties that are preferable over zinc gluconate for use in zinc lozenges. Zinc acetate dihydrate is 29.78% zinc compared with 13.14% zinc for zinc gluconate. Only 77.23 mg zinc acetate is needed to provide 23 mg zinc whereas 175 mg of zinc gluconate is needed. Over four hundred grams zinc acetate will dissolve in a liter of water compared to zinc gluconate at 100 grams/liter. The first stability constant of acetic acid (log $K_1$ 1.03) is lower than that of gluconic acid (log $K_1$ 1.64). The ready availability of zinc ions from zinc acetate is well known. Zinc acetate has been used in vitro by Bruce D. Korant (1974) to inhibit replication of rhinoviruses.

Surprising and unexpected flavor characteristics: Most importantly, very surprisingly and totally unexpectedly, with zinc acetate or zinc acetate diluted with any sweet, consumable, pharmaceutically acceptable carriers such as sweetened water, fructose, sucrose, dextrose, sweetened starch, sweetened lactose or other sweet dilutants, there is neither a long lasting aftertaste nor an offensive aftertaste like that present with zinc gluconate or other zinc compounds similarly formulated. This inventor also discovered that taste of zinc acetate is manageable with consumable, sweet pharmaceutically acceptable carriers such as fructose or sucrose; and eliminated with added super sweeteners like saccharine and various flavors; all of which is directly contrary to teaching of U.S. Pat. No. 4,684,528.

Fructose and sucrose as pharmaceutical carriers: Fructose is the sweetest of the natural sugars. It is a component of sucrose, a disaccharide, and is an isomer of dextrose. Neither fructose, sucrose nor dextrose are believed to chelate zinc in a way that would detract from its utility in treating common colds. It is surprising and unexpected that fructose does not visibly react, change color or form bitter compounds with zinc acetate at high summertime room temperatures as this monosaccharide is a polyhydroxy ketone and is usually considered highly reactive. On the other hand, glucose or dextrose, a polyhydroxy aldhyde is normally considered an inert monosaccharide. Yet, dextrose reacts with zinc gluconate over time to form bitter complexes, but not with zinc acetate. Since both acetic acid and gluconic acid are closely related monocarboxylic acids, it is strange and unforeseen that they would react differently. Sucrose and dextrose, but not fructose, react with primary amino acids such as glycine in presence of zinc turning brown and unattractive at high summer-time room temperatures over time. Various sweet tasting commercial tablet bases having a modified sugar base produced bitter zinc gluconate lozenges after aging for a few weeks to 2 months, particularly when exposed to summer temperatures. However, Mendell's Sugartab®, did not become bitter when used to make zinc acetate lozenges.

Favored compositions of fructose or sucrose with zinc acetate: It can now be revealed that preference is given to use of zinc acetate in a fructose based carrier over other sugars, and to zinc acetate over zinc gluconate. Favored form is zinc acetate in fructose lozenges. Generally lozenges are made in a 4 to 6 gram size to allow a suitable dissolution rate for lozenges. Dissolution rate should be about 12 to 15 minutes in water bath testers at 37 C. degrees or about 30 minutes when dissolved in the mouth as a lozenge, although there is considerable variability (fifteen minutes to one hour and fifteen minutes), depending on the amount of saliva produced in response to the lozenges. Smaller and bigger lozenges from 0.1 up to 15 grams were made and are anticipated by this invention. The majority of most lozenges, perhaps 50 to 90 percent, is pharmaceutical carrier.

Compressed tablet compositions: Lozenges, tablets and troches have essentially the same meaning for purposes of this invention. Since fructose is sweeter than sucrose, and other sugars, it is preferred for use in direct compression of lozenges containing zinc acetate. Fructose may be processed for direct compression of tablets, troches and lozenges by incorporation of a tablet binder such as PEG 6000 or 8000. To make directly compressible lozenges, add to processed fructose with zinc acetate, or add to other commercially available direct compression products such as Mendell's Sugartab® with zinc acetate, saccharin if desired, flavors as desired, glidants such as silica gel as needed, and lubricants such as magnesium stearate as needed. Mixture should be kept dry, preferably about 0.1 to 0.3% water. Ingredients are mixed together and directly compressed into lozenges, tablets or troches using conventional pharmaceutical mixing and tableting equipment. Store in air tight containers in a cool dark place. If heated to high summer-time room temperatures, compositions, when properly prepared, do not turn brown over time and do not have a bitter aftertaste, even if aromatic flavor oils are lost. If sufficient saccharine is included, no flavors are needed for compositions to have sweet pleasant tastes in addition to no zinc aftertaste.

Although added ingredients are not believed necessary to present a reasonably flavorful composition having essentially no zinc aftertaste, addition of super sweeteners, such as saccharine and any flavor is anticipated and suggested.

Liquid compositions: Zinc acetate with a sweet, consumable pharmaceutically acceptable carrier may be prepared in any liquid form such as syrups, mouth washes or sprays with water or other liquids for repeated delivery of concentrated ionizable zinc to oral and oral pharyngeal mucous membranes over a sustained period of time so as to permit a prolonged contact of ionizable zinc in the mouth.

Soft compositions: Zinc acetate in fructose or sucrose chewable compositions such as a soft candy, gum drop, liquid filled candies or chewing gum base may be prepared by adding zinc acetate and fructose or sucrose to said soft bases.

Super sweeteners: Various super sweeteners including saccharine, aspartame, cyclamates, monoammoniated glycerrhizins, neohesperidin dihydrochalcone and other super sweeteners may be added to the sweet, consumable pharmaceutically acceptable carrier as appropriate.

Flavors: Many flavorings can be added to impart their own flavor including but not restricted to anise, anethole, eucalyptol, wintergreen, licorice, clove, cinnamon, spearmint, cherry, lemon, orange, lime, menthol, peppermint and various combinations.

Stabilized flavors: Some flavor oils may not be stable in long-term storage in zinc acetate lozenges, and must be prevented from contacting zinc, evaporating and degrading generally. In lozenges and other dry solid compositions, flavors may be stabilized by spray drying with National Starch's N-Lok or other modified starches, or included within cyclodextrins, and/or coated with PEG 6000 or 8000. Spray dry flavors must not include acacia, a powerful zinc chelator. Zinc acetate may be coated with PEG 6000, 8000 or higher molecular weight PEG or included within cyclodextrins to prevent contact of zinc with flavors.

The favored method of stabilizing ingredients is by including them into cyclodextrin. Cyclodextrins molecules are toroidal, ring, annular, "bucket" or "doughnut" shaped having a hollow interior cavity. Alpha cyclodextrin has a 5.7 angstrom cavity. Beta cyclodextrin has a 7.8 angstrom cavity. Gamma cyclodextrin has a 9.5 angstrom cavity. Kleptose ® by Roquette, and Cavitron ® by American Maize-Product Company are examples of natural cyclodextrins suitable for said purpose. Modified cyclodextrins such as methylated, hydroxypropyl, polymeric may also be suitable. Beta-cyclodextrins may be the most useful of currently available cyclodextrins. It has been previously used to include flavor oils.

There are several practical methods of including flavor oils or zinc acetate into cyclodextrins. The slurry method involves addition of the guest ingredient to a warm thoroughly mixed aqueous slurry of cyclodextrin with thorough mixing, dewatering, drying and granulation.

Generally, interactions between the guest ingredient and cyclodextrins is by Van der Waals forces. The relation is not a chemical bond. Generally, one guest molecule fits into one cyclodextrin molecule. A macrocyclic structure, an hydrophilic exterior and a non-polar interior give cyclodextrins their very distinctive properties. The physical inclusion of the guest molecule is by displacement of water molecules from the cavity. The outer surface of the cyclodextrin molecule is hydrated, but the water molecules within the ring are in an energetically unfavorable position because of the non-polar surface of the molecular cavity. The potential guest molecule, such as anethole, repulses the water molecules. The result of the complex formation is that the non-polar side of the guest molecule penetrates into the non-polar cavity, thereby establishing an energetically favorable nonpolar-nonpolar interaction.

Inclusion results in essentially complete thermal, oxidative and photo-decomposition stability. Of particular interest, inclusion results in protection against oxidation otherwise accelerated by heat, light and metal salts.

This invention includes use of cyclodextrins to stabilize flavor oils in solid compositions containing zinc salts. Flavor oils are solidified in cyclodextrins, and become nonaromatic. Yet the full flavor of the oils is released in saliva from zinc lozenges made with flavor oils included in cyclodextrins. The flavors produced are truer, smoother and sweeter in taste than with out incorporation. Zinc taste and bitterness are reduced. Less flavor is needed with incorporation. The inclusion of flavor oils in cyclodextrins results in thermally stable flavor powders unaffected by high summertime temperatures. Inclusion of flavor oils in cyclodextrin essentially prevents evaporation of said oils nearly to the decomposition point of cyclodextrins at about 300 C. degrees. Such thermal, oxidative and photo-decomposition stability and protection against oxidation otherwise accelerated by heat, light and mental salts allows one to presume that the inclusion of flavor oils in cyclodextrins allows lozenges and other solid compositions to be stored for a much longer time that would otherwise be possible without lozenges losing their otherwise volatile flavor oils.

Preparation of flavor oils included in beta-cyclodextrin: Stoichiometric ratios of flavor oils and beta-cyclodextrins are mole per mole. The molecular weight of beta-cyclodextrin is 1135. The molecular weights of anethole, menthol, eucalyptus and methyl salicylate are respectively 148.21, 156.26, 154.24 and 152.14. Therefore, the amounts of the flavor oils included in beta-cyclodextrin is respectively 11.55%, 12.10%, 11.96% and 11.82%. For example, 12 mg anethole is in 104 mg of inclusion complex, 6 mg menthol is in 50 mg of inclusion complex, 3 mg of eucalyptol is in 25 mg of inclusion complex and 40 mg of methyl salicylate is in 338 mg of inclusion complex.

Pharmaceutically acceptable carriers: Without regard to desirability of ingredients or intended use of compositions, a more complete list of sweet, consumable, pharmaceutically acceptable carriers includes but is not limited to fructose, sucrose, sugar, dextrose, starch, mannitol, sorbitol, xylitol, lactose, maltose, maltodextrins, gluconolactones, corn syrup solids, honey solids, commercial tablet compositions such as Emdex, Mor-Rex, Royal-T, Di-Pac, Sugar-Tab, Sweet-Rex and others.

Undesirable ingredients for treating common colds: Zinc acetate compositions for treating common colds must exclude positively-charged-zinc ion-depleting ingredients and other incompatibles. Acacia, mannitol, sorbitol, artificial sweeteners, citric acid and other food acids, lake colors, alkalies and their carbonates, oxalates, phosphates, sulfides, lime water, and vegetable decoctions are usually incompatible with zinc acetate; and may cause compositions to be unstable or cause a loss of efficacy against common colds. Zinc ion depleting chelators must not be added in chemically significant amounts even if they are physically isolated from zinc acetate within compositions. Mannitol and sorbitol are common tablet bases which destroy beneficial properties of zinc lozenges in shortening common colds which must not be used in chemically significant amounts.

Examples of invented compositions: The following examples will serve to further illustrate, but not to limit, the present invention.

Favored zinc acetate lozenges can be prepared by direct compression of ingredients. To make a 5-gram fructose based lozenge containing 23 mg zinc, mix 77.2 mg zinc acetate dihydrate, saccharine (up to 50 mg if desired), about 104 mg anethole/beta-cyclodextrin complex or as desired, 100 mg magnesium stearate (lubricant) and sufficient directly compressible PEG prepared fructose to make a five gram lozenge. Compress with tablet press using sufficient pressure to obtain desired dissolution rate. About 6 tons of pressure using a hand press on a properly prepared ¾ inch diameter 5-gram lozenge results in a 12 to 15 minute dissolution rate in water bath testers. Such composition is thermally, chemically and flavor stable having a pleasant sweet taste and no unpleasant aftertaste.

To make a 5-gram fructose based lozenge containing 23 mg zinc, mix 77.2 mg zinc acetate dihydrate, saccharine (up to 50 mg if desired), about 60 mg anethole spray dried complex or as desired, 75 mg magnesium stearate and sufficient directly compressible PEG prepared fructose to make a five gram lozenge. Uncompressed powders and compressed lozenges are sweet and pleasant tasting with no aftertaste. Such composition is thermally, chemically and flavor stable having a pleasant sweet taste and no unpleasant aftertaste.

To make a 5-gram fructose based lozenge containing 23 mg zinc, mix 77.2 mg zinc acetate dihydrate, 75 mg magnesium stearate (lubricant) and sufficient directly compressible PEG prepared fructose to make a five gram lozenge. Compress with tablet press using sufficient pressure to obtain desired dissolution rate. Such composition, either in powder form or compressed solid form, is thermally, chemically and flavor stable having a reasonably acceptable taste and no unpleasant aftertaste.

To make a 5-gram sucrose based lozenge containing 23 mg zinc, mix 77.2 mg zinc acetate dihydrate, saccharine (up to 50 mg if desired), about 338 mg methyl salicylate/beta-cyclodextrin complex or as desired, 75 mg magnesium stearate (lubricant) and sufficient sucrose (such as Mendell Sugartab ®) to make a five gram lozenge. Compress with tablet press using sufficient pressure to obtain desired dissolution rate. Such composition, either in powder form or solid, is thermally, chemically and flavor stable having a pleasant wintergreen taste and no unpleasant aftertaste.

To make a 5-gram dextrose based lozenge containing 23 mg zinc, mix 77.2 mg zinc acetate dihydrate, saccharine (up to 50 mg if desired), about 338 mg methyl salicylate/beta-cyclodextrin complex or as desired, 100 mg magnesium stearate (lubricant) and sufficient dextrose to make a five gram lozenge. Compress with table press using sufficient pressure to obtain desired dissolution rate. Such composition is thermally, chemically and flavor stable having a pleasant taste and no unpleasant aftertaste.

To make a 5-gram lactose based lozenge containing 23 mg zinc, mix 77.2 mg zinc acetate dihydrate, saccharine (up to 50 mg if desired), about 140 mg anethole/beta-cyclodextrin complex or as desired, 75 mg magnesium stearate (lubricant) and sufficient directly compressible PEG prepared lactose to make a five gram lozenge. Compress with tablet press using sufficient pressure to obtain desired dissolution rate. Such composition is thermally, chemically and flavor stable having a pleasant taste and no unpleasant aftertaste.

To make a 5-gram maltose based lozenge containing 23 mg zinc, mix 77.2 mg zinc acetate dihydrate, saccharine (up to 50 mg if desired), about 140 mg anethole/beta-cyclodextrin complex or as desired, 75 mg magnesium stearate (lubricant) and sufficient directly compressible PEG prepared maltose to make a five gram lozenge. Compress with tablet press using sufficient pressure to obtain dissolution rate. Such composition is thermally, chemically and flavor stable having a pleasant taste and no unpleasant aftertaste.

To make a syrup wherein each 7.5 milliliter dose contains about 23 mg zinc from zinc acetate, add to 5 grams of deionized water, 2.5 grams of fructose or sucrose, 77.2 milligrams zinc acetate, saccharin if desired, and flavors complexed in water soluble cyclodextrins if needed and as desired. Vary amount of water and fructose to make other liquids such as mouth washes, gargles, and sprays. Such composition has a pleasant taste and no unpleasant aftertaste.

To make a chewing gum add to 4 grams of chewing gum base, about 5 grams of fructose, and 77.2 mg powdered zinc acetate, saccharin if desired and flavors complexed with cyclodextrins as desired. To make a soft candy, substitute soft candy for chewing gum base. Such compositions may be thermally, chemically and flavor stable having a pleasant taste and no unpleasant aftertaste depending upon other ingredients added.

COMMENTS AND OTHER EXAMPLES

Preferred zinc composition: The preferred zinc compound for use in flavor-stable zinc compositions having no unpleasant aftertaste for oral absorption is zinc acetate. The preferred method of applying zinc acetate to the oral mucosa is with fructose based lozenges. The preferred method to stabilize flavor oils is with cyclodextrins. All ingredients to be used in compositions within the present invention are consumable (meaning dissolvable, swallowable, suckable, chewable and so forth) and are believed safe for human consumption.

History: The first hard boiled candy lozenges using zinc acetate flavor masked with anethole were made by this inventor on Feb. 5, 1988. Adding zinc acetate to a hot molten candy base flavored with anethole caused large amounts of vapor to boil off hot compositions. Vapors had a strong vinegar odor. Anethole flavored compositions had a strong vinegar taste and odor without a zinc taste. Hard boiled zinc acetate lozenges were not made without anethole so discovery of this invention was not possible at that time.

First compressed lozenge examples of compositions were made on Aug. 29, 1989. They contained 86.98 mg zinc acetate dihydrate, 3260 mg fructose, 350 mg Mendell Sugartab ®, 67 mg sodium saccharin and 24 mg peppermint flavor. Said composition was both too sweet and too strongly peppermint flavored. Sealed compositions showed no loss of sweetness, degradation of flavor or unpleasant aftertaste over a storage period of well over one year under high temperature summer conditions. The chemically, thermally and flavor stable characteristics and absence of aftertaste were discovered by this inventor on Nov. 19, 1990. Another sample was made on Dec. 28, 1989. Compositions contained 64.5 mg zinc acetate, 14 mg saccharin, 4434 mg fructose, 500 mg PEG and flavors consisting of 12 mg anethole, 8, mg menthol and 6 mg eucalyptol plated onto silica gel. Compositions lost all of their flavor and anethole flavor mask over the following year, but were discovered by this inventor on Nov. 19, 1990 to have a pleasant taste and aftertaste. Zinc acetate and fructose or sucrose lozenges are believed to be chemically, thermally and flavor stable for over five years even when exposed to high room temperatures up to 55° C., degrees throughout each summer without development of bitter aftertastes. A flavor stable lozenge means that there is no increase in bitterness after manufacturer as may be found for zinc gluconate lozenges in sucrose. A flavored lozenge has the taste property of the individual added flavor, which may have considerable variability in stability depending upon the flavor stabilization method used.

Importance of Invention: Flavor-stable oral zinc compositions are important in that a soluble and ionizable zinc compound, zinc gluconate, has been demonstrated useful in lozenge form to shorten duration of common colds. Zinc acetate is more soluble and more ionizable than zinc gluconate, offering improved performance in treating common colds according to U.S. Pat. No. 4,956,385. Zinc acetate is known to be strongly antirhinoviral in vitro. Common colds often require oral zinc treatment about every two hours or so in order to shorten them by about 7 days. Highly palatable oral zinc compositions are needed as encouragement for a person in need of such treatment to continue treatment until symptoms are eliminated. Above examples serve to demonstrate that palatable zinc lozenges and other similar compositions without unpleasant aftertaste are possible using a fructose, sucrose or other sweet dilutent without amino acids of Godfrey and without anethole of Eby. The examples also show that compositions with stabilized flavors can retain their pleasant flavor for long, commercially interesting, periods of time.

Compositions may have not been observed previously because zinc acetate does not appear to have been used before for food or nutritional purposes as it is not considered Generally Accepted As Safe (GRAS). Perhaps such is because zinc acetate has a very bitter, offensive and vile taste leading those skilled in the art to avoid use of zinc acetate in food products.

Release rates: As will be apparent from examples, the amount of zinc ion which will be released can be controlled by the amount of zinc acetate incorporated in compositions. As will be readily understood, if a larger composition with a larger ratio of fructose or sucrose to zinc is used, that such is anticipated. Also, as will be readily understood, other release rates of zinc and fructose or sucrose are possible and anticipated. Any appropriate means of oral administration such as different size lozenges, hard molded candies, syrups, mouth washes, gargles, tablets, liquids, chewing gums, powders, sprays, and aerosols may be used and are anticipated. Any means suitable for delivery of zinc acetate and a consumable, sweet pharmaceutically acceptable carrier to oral and oral pharyngeal mucous membranes to permit a pleasant prolonged contact of zinc in the mouth may be used and is anticipated. Present invention provides pleasant new means of releasing zinc in the oral cavity, in various amounts, and at various rates determined by the formulation and composition used in a manner that is a substantial improvement in flavor, thermal and chemical stability over plain or otherwise flavored zinc compounds.

As will be apparent to one skilled in the art, variations can be made within the scope of the aforesaid description. Such variations being within the ability of one skilled in the art form a part of the present invention and are embraced by following claims.

I claim:

1. A composition for release of zinc ions to the oral and oral pharyngeal mucous membranes of a human consisting essentially of a sweet pharmaceutically acceptable carrier and contained in said carrier;

zinc acetate; and pharmaceutical necessities;

where said composition is slowly and uniformly released in the oral cavity as said composition is being orally consumed or masticated and whereby said composition is stable and has a pleasant taste and aftertaste.

2. The composition of claim 1 wherein said composition is a lozenge containing about 7 to 168 mg of zinc acetate dispersed in about 1 to 15 grams of sweet pharmaceutically acceptable carrier.

3. The composition of claim 1 wherein said composition is a compressed tablet containing about 7 to 168 mg of zinc acetate dispersed in about 1 to 15 grams of sweet pharmaceutically acceptable carrier.

4. The composition of claim 1 wherein said composition is a powder containing about 7 to 168 mg of zinc acetate dispersed in about 1 to 15 grams of sweet pharmaceutically acceptable carrier.

5. The composition of claim 1 wherein said composition is a liquid containing about 7 to 168 mg of zinc acetate dispersed in about 1 to 15 grams of sweet pharmaceutically acceptable carrier.

6. The composition of claim 1 wherein said sweet pharmaceutically acceptable carrier consists of fructose, sucrose, dextrose, maltose, maltodextrins, gluconolactones, corn syrups, honey solids, starch, lactose, water, and combinations thereof.

7. The composition of claim 1 wherein said pharmaceutical necessities consists of tablet binding agents, glidants, flavors other than anethole, chewing gum base, super sweeteners, and lubricants.

8. The composition of claim 1 wherein saccharin is employed as said super sweetener.

* * * * *